United States Patent [19]

Scales

[11] 4,185,341

[45] Jan. 29, 1980

[54] SUPPORT APPLIANCE

[75] Inventor: John T. Scales, Stanmore, England

[73] Assignee: The Institute of Orthopaedics, London, England

[21] Appl. No.: 5,878

[22] Filed: Jan. 23, 1979

Related U.S. Application Data

[63] Continuation of Ser. No. 848,520, Nov. 4, 1977, Pat. No. 4,136,413.

[30] Foreign Application Priority Data

Nov. 8, 1976 [GB] United Kingdom ............... 46432/76

[51] Int. Cl.$^2$ .......................... A47C 27/08; A61F 5/00

[52] U.S. Cl. ............................................ 5/461; 5/468; 5/482; 128/1 R

[58] Field of Search ........................ 5/90, 91, 347, 365; 128/1

[56] References Cited

U.S. PATENT DOCUMENTS

| | | | |
|---|---|---|---|
| 3,757,366 | 9/1973 | Saeher | 5/91 |
| 3,866,606 | 2/1975 | Hargest | 128/71 |
| 3,949,438 | 4/1976 | Scales | 5/91 |
| 4,057,861 | 11/1977 | Howarth | 5/91 |
| 4,136,413 | 1/1979 | Scales | 5/365 |

*Primary Examiner*—Casmir A. Nunberg

*Attorney, Agent, or Firm*—Cushman, Darby & Cushman

[57] ABSTRACT

A mattress of resilient foam has a separate cover formed from a chemically/physico-chemically porous material to transmit water/vapor on the outer side of the surface, due to differential water vapor pressure to within the mattress from which it can disperse.

2 Claims, 6 Drawing Figures

SUPPORT APPLIANCE

This is a continuation of application Ser. No. 848,520 filed Nov. 4, 1977, now U.S. Pat. No. 4,136,413.

BACKGROUND OF THE INVENTION

1. Field of the Invention.

This invention relates to support appliances and is particularly, although not exclusively applicable to mattresses, pillows and the like.

2. Description of the Prior Art.

My U.S. Pat. No. 3,822,425 discloses an air support appliance, for example, an air mattress which comprises an envelope of material which is inflated by air under pressure flowing continuously through the mattress. The surface material of at least the upper surface of the mattress is a material which is substantially impermeable to liquids and solids but is capable of transmitting water vapour when the water vapour partial pressure is higher on one side of the material than the other so that water vapour generated by the user of th bed passes through the upper surface of the mattress and is carried away with the continuous stream of air flowing through the mattress. A disadvantage with the air mattress described above is that air pressure is required not only to purge the mattress but also to support the user of the bed and this requires a substantial air pump. It is an object therefore of this invention to provide a construction of support appliance on which there is less dependence on air pressure for supporting the user of the appliance.

My U.S. Pat. No. 3,949,438 discloses a support appliance in the form of a mattress of a resilient foam material having interconnecting air transmitting cells and an upper surface which has at least an impedance to gas flow whilst permitting transmission of water vapour from the outer to the inner side thereof for removal by air flow through the mattress effected by an air pump. Here again it has been found that a substantial air pump with an elaborate system for controlling air temperature must be provided to ensure air flow through the mattress and to ensure that undue heating or cooling of the mattress which would cause discomfort to the user does not occur.

SUMMARY OF THE INVENTION

This invention provides a support appliance comprising a resilient air permeable body capable of supporting a user and a cover extending over at least that portion of body which supports the user, the cover comprising a material which is free waterproof but is chemically/-physicochemically porous to permit transmission of water vapour on the outside of said portion of the surface area to within the body and from which the water vapour can be dispersed when subjected to a differential water vapour pressure.

It has previously been understood that the water vapour pressure within the appliance should be lower than that on the outer surface in order to achieve transfer of water vapour through the surface. For that reason an air flow over the inner side of the surface of the appliance was thought to be necessary to maintain a low water vapour pressure on the inner side and that required a substantial air pump. It has now been found that the same effect can be achieved by increasing the water vapour pressure on the outer surface and this occurs naturally where the patients own body lies on the surface. Thus the water vapour produced by the patient from perspiration, transpiration or other insensible loss is automatically caused to pass through the surface of the support appliance without the assistance of air flow on the inner side due solely to the differential water vapour pressure.

DESCRIPTION OF THE PREFERRED EMBODIMENTS

Figure 1:
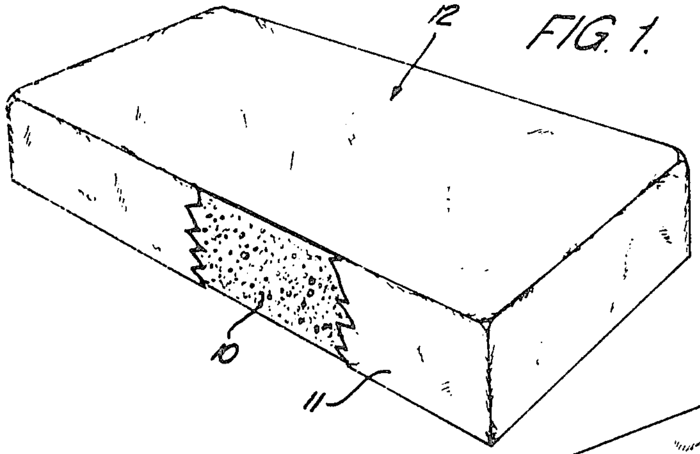
FIG. 1 is a perspective view of the upper side of a hospital bed mattress.
Figure 2:
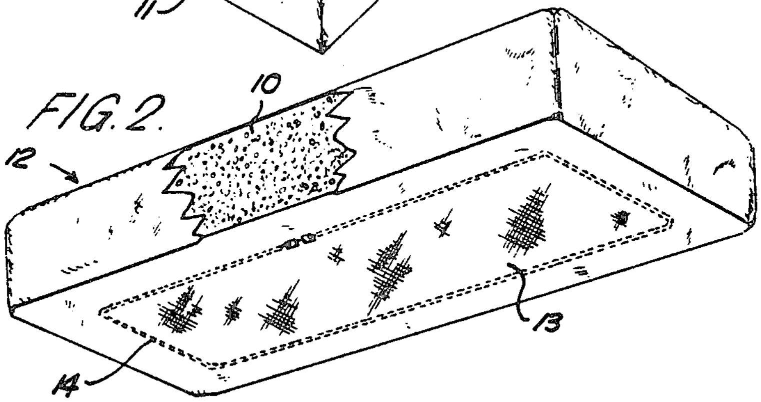
FIG. 2 is a perspective view of the under side of the mattress of FIG. 1.

The mattress shown in FIGS. 1 and 2 comprises a body 10 of resilient foamed material formed preferably from a polyether foam which has continuous inter-connected air-transmitting cells. The body could alternatively be any conventional air permeable mattress.

The body is fully enclosed by a cover 11 comprising a main part 12 which extends over the upper side and end surfaces and a subsidiary panel 13 which extends over the under side of the body. The subsidiary panel is attached to the main part of the cover by a zip or zips 14 so that the subsidiary panel can be removed from the main part and then the main part removed from the body for washing.

The main part of the cover is formed from a chemically/physico-chemically porous laminated material comprising a free waterproof polyurethane, silicon or vinyl co-polymer which transmits water vapour when subjected to a differential water vapour pressure. Such a material is described in British Patent Specification No. 1, 341,325 and is capable of transmitting about 230 grams per square meter per 24 hours at 37° C., and at a Relative Humidity of not more than 50%. The film is laminated by a suitable agent on a nylon one-way or two-way stretch base layer. The laminated material permits the passage of water vapour through the material at locations where pressure is applied to the material by the user of the bed but is not permeable to solids or liquids. Carbon dioxide may also be transmitted through the material in a similar way to the water vapour.

The subsidiary panel of the cover is formed from a physically porous material such as nylon or terylene.

Water vapour released by the user of the bed passes through the laminated material into the foam body and is transmitted to the cells of the foam body to the underside of the body by the normal motion of the user on the body. The water vapour released at the under side of the body can permeate through the porous subsidiary panel of the cover and thence escape to atmosphere. In order to permit the release of water vapour from the under side of the mattress, the mattress must be used on a bed having a mattress support which has an open grid-like structure.

Figure 3:
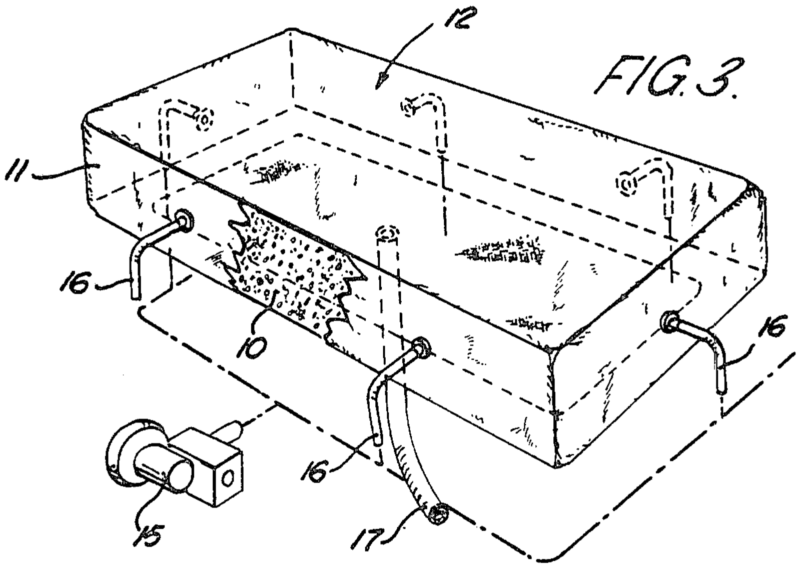
FIGS. 3 to 6 show further arrangements.

FIG. 3 of the drawings shows a modified arrangement in which the water vapour in the resilient air permeable body is purged by an air-flow through the body. An air pump is indicated at 15 which supplies air to the sides of the body through ducts 16. The inlet ducts are spaced around the periphery of the body to provide an air-flow through all parts of the body. An outlet duct 17 is provided at the centre of the underside of the body to vent air from the body.

In this case the subsidiary panel of the cover is formed from a non-porous material and an air-tight zip is used so that air can only be released from the mattress through the outlet duct. The air pressure supplied to the body to purge the body is such that little or no inflation of the body occurs. Typically the pressure will be up to 8 inches water gauge. The air supply to the mattress may be at room temperature or may be warmed by a heater arranged in the air inlet system.

In a modification of the arrangement shown in FIG. 3, the outlet of the air pump 15 is connected to the conduit 17 to supply air to the centre of the resilient body 10 and the cover 11 has outlets spaced along the side and end walls to permit escape of air from the body. Outlet conduits may be connected to the outlets to exhaust the air to atmosphere at a required location away from the mattress.

Figure 4:
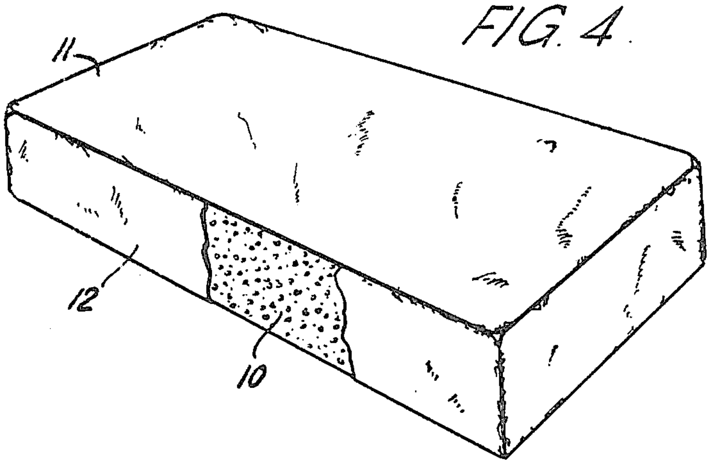
Figure 5:
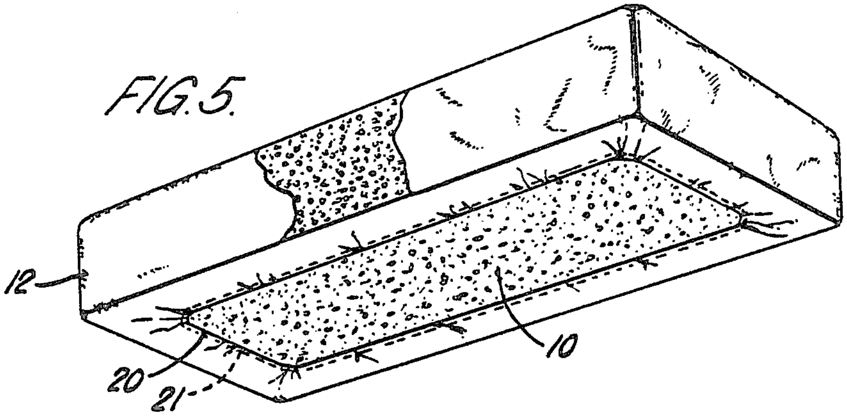

FIGS. 4 and 5 of the drawings show a mattress which comprises a body 10 of a resilient foamed material formed preferably from a polyether foam which has continuous interconnected air transmitting cells. LThe body could alternatively be any conventional air permeable mattress.

The body is enclosed by a cover 11 which extends over the upper side of the mattress and has a skirt 12 encircling the periphery of the mattress, the lower part of the skirt extending underneath the mattress as best seen in FIG. 2 and having a hem 20 within which a length of elastic 21 extends to hold the skirt against the mattress.

The cover is formed, as before, from a chemically porous laminated material comprising a water vapour permeable polyurethane, silicon or vinyl copolymer resin which allows the passage of water vapour at a rate of at least about 230 grams per square meter per twenty-four hours at 37° C., at a Relative Humidity of not more than 50%. The film is laminated by a suitable agent on a nylon one-way or two-way stretch base layer. The laminated material permits the passage of water vapour through the material at locations where pressure is applied to the material by the user of the bed but is not permeable to solids or liquids. Carbon dioxide may also be transmitted through the material in a similar way to the water vapour. The water vapour enters the air permeable mattress, is dispersed through the mattress and can eventually evaporate from the exposed part of the underside of the mattress.

Figure 6:
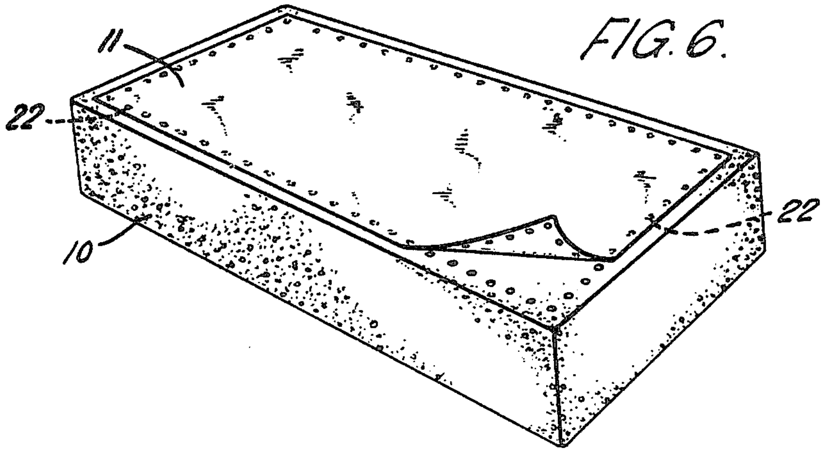

The modified bed cover 11 shown in FIG. 6 of the drawings extends over the upper side of the mattress 10 only and is attached to the surface of the mattress to hold it in place by spaced press-studs 22 around the periphery of the cover and the periphery of the mattress.

I claim:

1. A method of using a support appliance, which appliance comprises a resilient air permeable body capable of supporting a user, and a cover extending over at least that portion of the body which supports the user, the cover comprising a material which is free-water proof but is chemically/physico-chemically porous to permit transmission of gaseous water vapour on the outside of said portion of the surface area to within the body and from which the water vapour can be dispersed when subjected to a differential water vapour pressure, said method comprising supporting a user on said appliance and relying solely on the effects of the weight and movements of the user thereupon to cause said transmission and dispersal of gaseous water vapour.

2. A method of using a support appliance which appliance comprises a resilient air permeable body, a covering extending over at least that portion of the body which supports the user, the cover comprising a material which is free-water proof but is chemically/-physico-chemically porous to permit transmission of gaseous water vapour on the outside of said portion of the surface area to within the body and from which the water vapour can be dispersed when subjected to a differential water vapour pressure, and means for supplying a flow of gas through the body, said method comprising supporting a user on said appliance, activating said gas supply means but without inflating said body, relying only on the effects of the weight and movement of the user upon said body, together with said gas flow therethrough to cause said transmission and dispersal of gaseous water vapour.

* * * * *